United States Patent [19]  [11] Patent Number: 4,617,313
Bigg et al.  [45] Date of Patent: Oct. 14, 1986

[54] ALPHA$_2$-ANTAGONISTIC 2-(4,5-DIHYDRO-1H-IMIDAZOL-2-YL)-PYRROLO[3,2,1-HI]INDOLES

[75] Inventors: Dennis Bigg, Jouy en Josas; Claude Morel, Magny-les-Hameaux; Mireille Sevrin, Paris, all of France

[73] Assignee: Synthelabo, France

[21] Appl. No.: 770,079

[22] Filed: Aug. 28, 1985

Related U.S. Application Data

[63] Continuation-in-part of Ser. No. 680,504, Dec. 11, 1984, abandoned.

[30] Foreign Application Priority Data

Dec. 12, 1983 [FR] France ............................. 83 19850
Sep. 27, 1984 [FR] France ............................. 84 14839

[51] Int. Cl.$^4$ .................. A61K 31/415; C07D 487/06
[52] U.S. Cl. ...................................... 514/402; 548/348
[58] Field of Search ...................... 548/348; 514/402

[56] References Cited

U.S. PATENT DOCUMENTS 3,671,541  6/1972  Bormann et al. ............... 548/348
4,391,814  7/1983  Vorbruggen ..................... 548/348
4,411,908 10/1983  Chapleo et al. ................. 548/348

Primary Examiner—Richard A. Schwartz
Assistant Examiner—Kurt G. Briscoe
Attorney, Agent, or Firm—Wegner & Bretschneider

[57] ABSTRACT

Pyrrolo[3,2,1-hi]indole derivatives, in the form of racemates or optically active isomers, of formula (I)

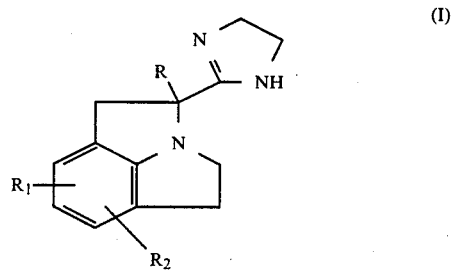

in which R is a hydrogen atom or $C_1$–$C_4$ alkyl and $R_1$ and $R_2$, which may be the same or different, are hydrogen, halogen or $C_1$–$C_4$ alkyl and their pharmaceutically acceptable acid addition salts are useful as $\alpha_2$-antagonists.

4 Claims, No Drawings

ALPHA₂-ANTAGONISTIC 2-(4,5-DIHYDRO-1H-IMIDAZOL-2-YL)-PYRROLO[3,2,1-HI]INDOLES

This application is a continuation-in-part of copending application Ser. No. 680,504, filed Dec. 11, 1984, now abandoned.

The present invention relates to pyrroloindole derivatives, their preparation and pharmaceutical compositions containing them.

The invention provides pyrrolo[3,2,1-hi]indole derivatives, in the form of racemates or optically active isomers, of the formula (I)

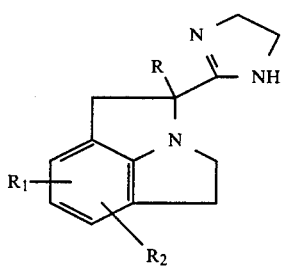

in which R is hydrogen or a linear or branched $C_{1-4}$ alkyl group, and $R_1$ and $R_2$ which may be the same or different, are hydrogen, halogen or $C_{1-4}$ alkyl, and their pharmaceutically acceptable acid addition salts.

According to the invention, the compounds (I) can be prepared by following the reaction scheme given in the Appendix.

The starting ester (II), in which R' is an alkyl group, in particular ethyl, can be obtained from N-aminoindole according to the method described by H. Rapoport et al. (J.A.C.S. [1958], 80, 5574–5), the N-aminoindole itself being prepared according to the method described by A. N. Kost et al. (C.A. 54, 1964).

According to the invention, the starting ester (II) is hydrogenated by means of hydrochloric acid in the presence of tin at ambient temperature to provide a compound (III).

Then
either the compound (III) is reacted with ethylenediamine in the presence of trimethylaluminium to obtain a compound (I) in which R is hydrogen,
or the compound (III) is alkylated by reaction with an alkyl halide RX, in which R is $C_1$-$C_4$ alkyl and X is halogen (preferably iodine), for example in the presence of diisopropylamine and butyllithium in a solvent, and the alkylated compound (IV) thus obtained is reacted with ethylenediamine in the presence of trimethylaluminium to obtain a compound (I) in which R is a $C_1$-$C_4$ alkyl group. The compound (I) thus obtained can be converted into an acid addition salt by any known method.

The Examples which follow illustrate the invention. The structure of the compounds obtained was confirmed by analysis and IR and NMR spectra.

EXAMPLE 1

2-(4,5-Dihydro-1H-imidazol-2-yl)-1,2,3,4,5-tetrahydropyrrolo[3,2,1-hi]indole and its fumarate.

1. In a 1,000-ml three-necked flask equipped with a magnetic stirrer, hydrogen chloride gas inlet, air-cooled condenser with calcium chloride guard tube and thermometer, placed in a bath of dry ice and isopropyl alcohol, 15.8 g (0.073 mol) of ethyl 4,5-dihydropyrrolo[3,2,1-hi]indole-2-carboxylate are introduced with 150 ml of ethanol.

The mixture is cooled to −20° C. and hydrogen chloride gas is condensed in at this temperature until a solution is obtained. 26.1 g (0.22 gram-atom) of granulated tin are then added in a single portion, the cold bath is removed and stirring is maintained for 20 hours at room temperature.

A yellow suspension is obtained, and this is concentrated on the water bath and taken up in 550 ml of absolute ethanol. The mixture is cooled, ammonia is bubbled in until the pH equals 9 to 10 to precipitate the tin salts, the latter are drained while being washed with iced ethanol and the filtrate obtained is evaporated to dryness. The residue is subjected to chromatography on a silica column, eluting with methylene chloride. 11.65 g of an oily yellow product are finally collected.

2. In a 100-ml Keller flask equipped with a magnetic stirrer, reflux condenser with calcium chloride guard tube, thermometer, argon inlet, dropping funnel and Dean-Stark apparatus, there are successively introduced, under argon, 16 ml of toluene, 10.3 ml (0.025 mol) of trimethylaluminium at 25.2% strength in hexane and, while cooling, 1.6 ml (equivalent to 1.43 g or 0.024 mol) of ethylenediamine dissolved in 4.5 ml of toluene.

The mixture is stirred for 5 minutes and then heated to 50° C., and at this temperature there are added 3.3 g (0.015 mol) of the product previously obtained, dissolved in 15 ml of toluene. The mixture is then heated under reflux for 6 hours and then allowed to cool. After the mixture has been cooled to between −10° and −15° C., it is hydrolysed with 10.2 ml of water while stirring, and is then extracted with ethyl acetate. The organic fractions are combined, washed with sodium chloride solution, dried, filtered and evaporated. There remain approximately 3 g of a fatty yellow solid from which the fumarate is prepared directly. For this purpose, the solid is taken up in 50 ml of ethanol and the solution is filtered, and a filtered solution of 1.5 g (0.013 mol) of fumaric acid in 100 ml of ethanol is added to it. The solution obtained is stirred and concentrated to dryness, and the residue is taken up in acetone, filtered, dried under vacuum and recrystallised in ethanol. 1.65 g of the fumarate is collected which melts at 184.5°–186° C.

EXAMPLE 2

2-Methyl-2-(4,5-dihydro-1H-imidazol-2-yl)-1,2,4,5-tetrahydropyrrolo[3,2,1-hi]indole and its fumarate

2.1. Ethyl 2-methyl-1,2,4,5-tetrahydropyrrolo[3,2,1-hi]indole-2-carboxylate

In a 250-ml Keller flask equipped with a magnetic stirrer, thermometer, argon inlet and dropping funnel and placed in a cold bath, there are introduced, under argon, 5.6 ml (0.04 mol) of diisopropylamine and 35 ml of tetrahydrofuran (THF). The reaction mixture is cooled to between −70° and −75° C. and there are then introduced, in the course of 20 minutes, 25 ml (0.04 mol) of butyllithium in 1.6 molar solution in hexane.

The temperature is maintained at between −70° and −75° C. for 1 hour, and a solution of 7 g (0.0322 mol) of ethyl 1,2,4,5-tetrahydropyrrolo[3,2,1-hi]indole-2-carboxylate in 25 ml of THF is added in the course of 15 minutes.

The temperature is still maintained at between −70° and −75° C. for 1 hour and a solution of 12.4 ml (0.2 mol) of methyl iodide in 20 ml of THF is then added in the course of 20 minutes.

The reaction mixture is maintained at between −70° and −75° C. for 1 hour, and then left at room temperature for 3 hours 30 minutes. The reaction mixture is poured into iced water. It is extracted with diethyl ether in the presence of saturated sodium chloride solution. The extract is washed with water and dried over $NA_2SO_4$. The organic phase is separated. It is evaporated to dryness under vacuum on the water bath. An oil is obtained which is purified by passage through a silica column with methylene chloride as eluent.

2.2. 2-Methyl-2-(4,5-dihydro-1H-imidazol-2-yl)-1,2,4,5-tetrahydropyrrolo[3,2,1-hi]indole and its fumarate In a 50-ml Keller flask equipped with a magnetic stirrer, reflux condenser, thermometer, argon inlet, dropping funnel and Dean-Stark apparatus, there are introduced successively, under argon, 10 ml of toluene, 5.4 ml (0.013 mol) of trimethylaluminium at 25.2% strength in hexane and, while cooling to 0° C., 0.9 ml (equivalent to 0.013 mol) of ethylenediamine dissolved in 3 ml of toluene.

The mixture is stirred for 10 minutes and then heated to 50° C., and at this temperature there is added 1.9 g (0.0082 mol) of the product previously obtained, dissolved in 10 ml of toluene. The mixture is then heated under reflux for 6 hours and then allowed to cool. After the mixture has been cooled to between −10° and −15° C., it is hydrolysed with 5.4 ml of water, while being stirred, and is then extracted with ethyl acetate. The organic fractions are combined, washed with sodium chloride solution, dried, filtered and evaporated. There remains a yellow solid from which the fumarate is prepared directly.

For this purpose the solid is taken up in 25 ml of ethanol and the solution is filtered, and a filtered solution of 0.7 g (0.006 mol) of fumaric acid in 50 ml of ethanol is added to it. The solution obtained is stirred and concentrated to dryness, and the residue is taken up in acetone, filtered, dried under vacuum and recrystallised in ethanol. The fumarate is collected which melts at 192°–194° C.

EXAMPLE 3

2-n-Propyl-2-(4,5-dihydro-1H-imidazol-2-yl)-7-methyl-1,2,4,5-tetrahydropyrrolo[3,2,1-hi]indole and its fumarate.

3.1. 5-Methyl-1-nitroso-2,3-dihydro-1H-indole

In a 500-ml three-necked flask equipped with a magnetic stirring system, there are introduced 5-methyl-2-indoline (prepared according to G. W. Gribble and J. H. Hoffman, Synthesis, 1977, 859–860 from indole, described by J. E. Nordlander et al. J. Org. Chem. 46, 778–782, [1981]) to the extent of 18 g (0.14 mol) and 300 ml of 20% sulphuric acid.

The solution is cooled to 0° C. and sodium nitrite (9.7 g; 0.14 mol) dissolved in water (30 ml) is added. The reaction mixture is maintained at 0° C. during the addition.

After 30 minutes of stirring at 0° C., the aqueous phase is extracted with ether (500 ml). The ether phase is washed with water and then with saturated NaCl solution and dried over magnesium sulphate. The solvents are evaporated under vacuum. The compound obtained is used, as it is, in the following stage.

3.2. 5-Methyl-2,3-dihydro-1H-indol-1-amine

In a 2-l three-necked flask equipped with a mechanical stirring system, condenser, dropping funnel and thermometer, and under argon, there are introduced lithium aluminum hydride (6.08 g; 0.16 mol) and tetrahydrofuran (THF) (300 ml). The compound obtained above (22 g; 0.14 mol), dissolved in THF (300 ml) is added to the suspension. The temperature is maintained at 35° C.

The reaction mixture is stirred for 4 hours at 20° C. and then hydrolysed ($H_2O$, 10 ml). 10 ml of 1N NaOH solution are then added, followed by 20 ml of water.

The suspension is stirred at 20° C. for 30 minutes, then filtered and the residue rinsed with ether. The organic phase is dried over sodium sulphate. The solvents are evaporated under vacuum. The compound obtained is used, as it is, in the following stage.

3.3. Ethyl 2-([5-methyl-2,3-dihydro-1H-indol-1-yl]imino)-propanoate

In a 500-ml single-necked flask equipped with a magnetic stirring system and condenser, and under argon, there are introduced the above compound (20 g; 0.13 mol), ethyl pyruvate (16.24 g; 0.14 mol), ethanol (200 ml) and acetic acid (0.5 ml).

The reaction mixture is stirred at 80° C. for 5 hours. The ethanol is evaporated under vacuum and the residue is purified by column chromatography ($SiO_2$; eluent, cyclohexane/ether 2:1). The compound obtained is used, as it is, in the following stage.

3.4. Ethyl 7-methyl-4,5-dihydropyrrolo[3,2,1-hi]indole-2-carboxylate

In a 25-ml three-necked flask equipped with a magnetic stirring system and condenser, and under argon, there are introduced the compound obtained above (7 g; 0.028 mol) and acetic acid (8 ml), and $BF_3$ etherate (3.42 ml; 0.028 mol) is added. The reaction mixture is stirred at 90° C. for 50 minutes. It is cooled and hydrolysed ($H_2O$, 40 ml). The aqueous phase is extracted with ether (3×200 ml). The organic phase is washed with sodium bicarbonate, and with saturated sodium chloride solution, and then dried over sodium sulphate.

The solvents are evaporated under vacuum and the residue is purified by column chromatography ($SiO_2$; eluent, cyclohexane/ether 2:1). The ester (II) obtained is used in the following stage.

3.5. Ethyl 7-methyl-1,2,4,5-tetrahydropyrrolo[3,2,1-hi]indole-2-carboxylate In a 50-ml three-necked flask equipped with a magnetic stirring system and condenser, ethanol (21 ml) is introduced. The ethanol is saturated with hydrochloric acid at −10° C. The ester obtained above (2.4 g; 0.011 mol) is added, followed by tin (3.8 g; 0.032 g-atom). The reaction mixture is stirred at +20° C. for 8 hours. The solvent is evaporated under vacuum and the residue is dissolved in ethanol (50 ml). The mixture is saturated with ammonia until the pH equals 9. The suspension is filtered and the ethanol is evaporated under vacuum. The residue is dissolved in water and the aqueous phase is extracted with ether (300 ml); the ether phase is washed with saturated sodium chloride solution and then dried over sodium sulphate.

The ester (III) is obtained.

3.6. Ethyl 2-n-propyl-7-methyl-1,2,4,5-tetrahydropyrrolo[3,2,1-hi]indole-2-carboxylate In a 500-ml three-necked flask equipped with a magnetic stirring system and under argon, there are introduced diisopropylamine (0.600 g; 0.006 mol) and THF (5 ml). The solution is cooled to −78° C. and n-butyllithium is added to hexane (3.75 ml; 0.006 mol). The solution is stirred at −78° C. for 30 minutes, and the ester obtained above (III) (1.15 g; 0.005 mol) is then added in THF (10 ml). The reaction mixture is stirred at −78° C. for 1 hour (brown coloration). 1-Iodopropane (1.02 g; 0.006 mol) in THF (5 ml) is added.

The reaction mixture is stirred at −78° C. for 1 hour and then at 20° C. for 1 hour. The mixture is hydrolysed (H$_2$O, 10 ml). The aqueous phase is extracted with ether. The ether phase is washed with water and with saturated sodium chloride solution, and is then dried over sodium sulphate. The ester obtained (IV) is used in the following stage.

3.7. 2-n-Propyl-2-(4,5-dihydro-1H-imidazol-2-yl)-7-methyl-1,2,4,5-tetrahydropyrrolo[3,2,1-hi]indole and its fumarate a. In a 50-ml three-necked flask equipped with a magnetic stirring system and condenser, and under argon, there are introduced toluene (10 ml) and trimethylaluminium at 25% strength in hexane (4.5 ml; 0.011 mol). The solution is cooled to −10° C. and ethylenediamine (0.640 g; 0.011 mol) in toluene (5 ml) is then added. The reaction mixture is allowed to return to 20° C. and the ester (IV) obtained in 3.6 (1.22 g; 0.0044 mol) is added in toluene (10 ml).

The reaction mixture is stirred at 110° C. for 4 hours. It is cooled to −10° C. and then hydrolysed (H$_2$O, 5 ml), and ethyl acetate (50 ml) is added. The mixture is stirred for 30 minutes at 0° C. and then filtered. The filtrate is dried over Na$_2$SO$_4$. The solvents are evaporated under vacuum. The fumarate is prepared directly.

b. In a 250-ml single-necked flask equipped with a magnetic stirring system, the compound obtained in a. is introduced in ethanol (20 ml), and fumaric acid (0.500 g; 0.0042 mol) in ethanol (30 ml) is added. The solution is stirred for 30 minutes, and the ethanol is then evaporated under vacuum. The residue is taken up in ether. It is filtered, dried under vacuum and recrystallised in ethanol. The fumarate is collected which melts at 178°–180° C.

The Table which follows illustrates compounds prepared according to the invention.

TABLE

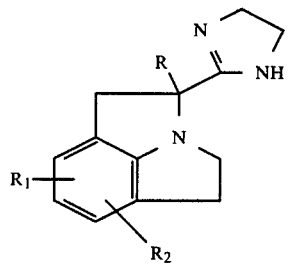

(I)

| Compound | R$_1$ | R$_2$ | R | Salt | M.p. (°C.) |
|---|---|---|---|---|---|
| 1 | H | H | H | fumarate | 184–186 |
|   |   |   |   | benzoate | 146–148 |
| 2 | H | H | CH$_3$ | fumarate | 192–194 |
| 3 | H | H | C$_2$H$_5$ | fumarate | 162–164 |
| 4 | H | H | nC$_3$H$_7$ | fumarate | 202–204 |
| 5 | H | H | nC$_4$H$_9$ | fumarate | 171–173 |
| 6 | 8-Cl | H | H | fumarate | 195–196 |
|   |   |   |   | hydrochloride | 268–270 |
| 7 | 8-Cl | H | CH$_3$ | fumarate | 94–99 |
| 8 | 8-Cl | H | nC$_3$H$_7$ | fumarate | 202–204 |
| 9 | 7-F | H | H | fumarate | 137–141 |
| 10 | 7-F | H | CH$_3$ | fumarate | 147–150 |
| 11 | 7-F | H | nC$_3$H$_7$ | fumarate | 200–203 |
| 12 | 7-CH$_3$ | H | H | fumarate | 168–172 |
| 13 | 7-CH$_3$ | H | nC$_3$H$_7$ | fumarate | 178–180 |
| 14 | 6-CH$_3$ | 8-CH$_3$ | H | fumarate | 217–219 |
| 15 | 6-CH$_3$ | 8-CH$_3$ | CH$_3$ | fumarate | 207–210 |
| 16 | 6-CH$_3$ | 8-CH$_3$ | nC$_3$H$_7$ | fumarate | 180–185 |
| 17 | 8-Cl | H | C$_2$H$_5$ | fumarate | 171–173 |
|   |   |   |   | hydrochloride | 285–287 |
| 18 | 8-F | H | H | fumarate | 174–176 |
|   |   |   |   | hydrochloride | 261–263 |
| 19 | 8-F | H | CH$_3$ | hydrochloride | 256–258 |
| 20 | 8-F | H | nC$_3$H$_7$ | fumarate | 186–188 |
| 21 | 6-Cl | H | H | fumarate | 165–170 |
|   |   |   |   | hydrochloride | 274–277 |
| 22 | 6-Cl | H | CH$_3$ | hydrochloride | 275–277 |
| 23 | 6-Cl | H | nC$_3$H$_7$ | hydrochloride | 246–248 |
| 24 | 6-CH$_3$ | H | H | fumarate | 217–222 |
| 25 | 6-CH$_3$ | H | nC$_3$H$_7$ | fumarate | 171–175 |
| 26 | H | H | iC$_4$H$_9$ | fumarate | 180–183 |

The compounds of the invention were subjected to pharmacological tests which showed their value as $\alpha_2$-antagonists.

To this end, the compounds were studied in the test of potentiality and selectivity of antagonists towards $\alpha_2$-receptors in vitro.

Determination of the pA$_2$ value in respect of the inhibitory effects of clonidine, a well-known $\alpha_2$-agonist, was carried out on rat vas deferens stimulated at a frequency of 0.1 Hz in the presence of 30 nM prazosin and 1 μM cocaine, according to the method described by G. M. Drew (European Journal of Pharmacology, 42, (1977) 123–130).

The pA$_2$ of the compounds of the invention are between 7 and 9.5.

The compounds of the invention are powerful $\alpha_2$-antagonists which can be used for the treatment of depression (either alone or in association with a product which inhibits neuronal uptake mechanisms), hypotension, post-operative paralytic ileum, asthma and obesity.

The pharmaceutical compositions can be in a form suitable for oral, rectal or parenteral administration, for example in the form of capsules, tablets, pellets, gelatine capsules or solutions, syrups or suspensions to be taken orally, and can contain suitable excipients.

The daily dosage can range from 0.1 to 10 mg/kg p.o.

Appendix

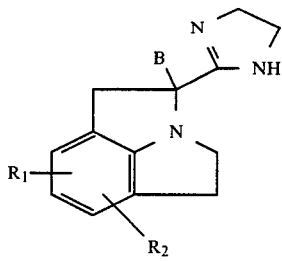

Reaction scheme

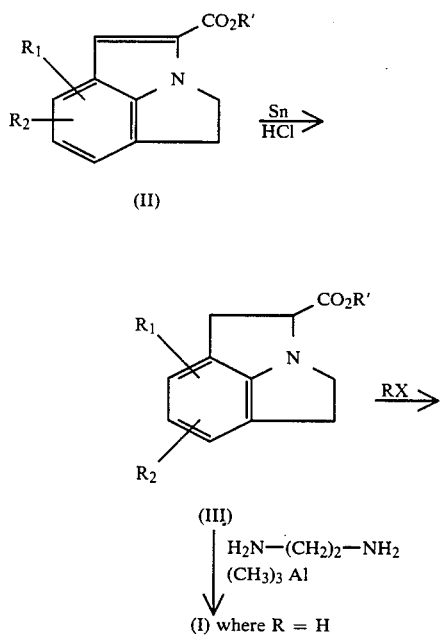

R' = alkyl, preferably ethyl
X = halogen, preferably I

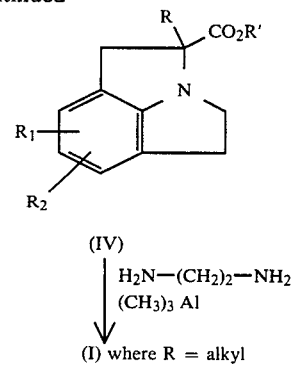

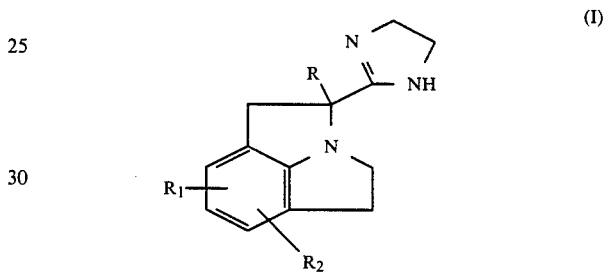

(I) where R = alkyl

We claim:

1. A pyrrolo-3,2,1-hi]indole derivative, in the form of the racemate or an optically active isomer, of the formula (I)

in which R is hydrogen or a linear or branched $C_{1-4}$ alkyl group, and $R_1$ and $R_2$ which may be the same or different, are hydrogen, halogen or $C_{1-4}$ alkyl, or a pharmaceutically acceptable acid addition salt thereof.

2. The pyrrolo-indole derivative of claim 1, wherein R is methyl, ethyl, n-propyl or n-butyl.

3. The pyrrolo-indole derivative of claim 1 wherein $R_1$ and $R_2$, which may be the same or different, are hydrogen, chlorine, fluorine, methyl, ethyl, n-propyl or n-butyl.

4. A pharmaceutical composition useful as an $\alpha_2$-antagonist which contains, as active ingredient, an $\alpha_2$-antagonistically effective amount of a pyrrolo-indole derivative or salt as claimed in claim 1, in association with a pharmaceutically acceptable excipient.

* * * * *